United States Patent
Morris et al.

(10) Patent No.: US 12,195,807 B2
(45) Date of Patent: Jan. 14, 2025

(54) METHOD OF TREATING A CANCER PATIENT WITHOUT THE NEED FOR A TISSUE BIOPSY

(71) Applicant: Inivata Ltd., Cambridge (GB)

(72) Inventors: Clive Morris, Cambridge (GB); Vincent Plagnol, Cambridge (GB); Tim Forshew, Stevenage (GB)

(73) Assignee: INIVATA LTD., Cambridge (GB)

( * ) Notice: Subject to any disclaimer, the term of this patent is extended or adjusted under 35 U.S.C. 154(b) by 0 days.

(21) Appl. No.: 17/831,345

(22) Filed: Jun. 2, 2022

(65) Prior Publication Data

US 2022/0364186 A1 Nov. 17, 2022

Related U.S. Application Data

(63) Continuation of application No. 16/560,504, filed on Sep. 4, 2019, now Pat. No. 11,377,698.

(60) Provisional application No. 62/727,462, filed on Sep. 5, 2018.

(51) Int. Cl.
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 10,329,627 B1 | 6/2019 | Beeler et al. | |
| 11,186,878 B2 | 11/2021 | Beeler et al. | |
| 2005/0272083 A1* | 12/2005 | Seshagiri | A61K 31/19 514/249 |
| 2014/0288116 A1 | 9/2014 | Bandla et al. | |
| 2014/0296081 A1 | 10/2014 | Diehn et al. | |
| 2015/0368725 A1* | 12/2015 | Ho | C12Q 1/6886 514/789 |

(Continued)

OTHER PUBLICATIONS

Oden-Gangloff et al .British Journal of Cancer. 100: 1330-1335 (Year: 2009).*

(Continued)

*Primary Examiner* — Carla J Myers
(74) *Attorney, Agent, or Firm* — James S. Keddie; Bozicevic, Field & Francis LLP

(57) ABSTRACT

Provided herein, among other things, is a method of treating a cancer patient without the need for a tissue biopsy. In some embodiments, the method may comprise (a) performing or having performed a sequencing assay on cell-free DNA (cfDNA) from a sample of blood from the patient to determine if the cell-free DNA comprises actionable and/or non-actionable sequence variations in one or more target genes, and (b) treating the patient using the following method: i. administering a therapy that is targeted to an actionable sequence variation if the patient is identified as having the actionable sequence variation, and ii. administering a non-targeted therapy in the absence of any follow-up genetic testing on DNA extracted from a tissue biopsy if one or more non-actionable sequence variations and no actionable sequence variations are identified.

8 Claims, 5 Drawing Sheets

(56) References Cited

U.S. PATENT DOCUMENTS

2021/0040564 A1    2/2021    Beeler et al.

OTHER PUBLICATIONS

Cisowski et al., "What makes oncogenes mutually exclusive?", Small Gtpases, 2016, 8(3): 187-192.

Ding et al., "Somatic mutations affect key pathways in lung adenocarcinoma", Nature, 2008, 455(7216): 1069-1075.

Koivunen et al., "Mutations in the LKB1 tumour suppressor are frequently detected in tumours from Caucasian but hot Asian lung cancer patients", British Journal of Cancer, 2008, 99: 245-252.

Leiserson et al., "A weighted exact test for mutually exclusive mutations in cancer", Bioinformatics, 2016, 32: i736-i745.

Sparks et al., "Mutational Analysis of the APC/β-Catenin/Tcf Pathway in Colorectal Cancer", Cancer Research, 1998, 58: 1130-1134.

Tam et al., "Distinct Epidermal Growth Factor Receptor and KRAS Mutation Patterns in Non^ Small Cell Lung Cancer Patientswith Different Tobacco Exposure and Clinicopathologic Features", Clin Cancer Res, 2006, 12(5): 1647-1653.

Bardelli et al., "Liquid Biopsies, What We Do Not Know (Yet)", Cancer Cell, 2017, 31:172-179.

Crowley et al., "Liquid biopsy: monitoring cancer-genetics in the blood", Nature Reviews Clinical Oncology, 2013, 10:472-484.

Durendez-Saez et al., "New insights in non-small-cell lung cancer: circulating tumor cells and cell-free DNA", Journal of Thoracic Disease, 2017, 13:S1332-S1345.

Ettinger et al., "Non-Small Cell Lung Cancer, Version 5.2017", Journal of the National Comprehensive Cancer Network, 2017, 15(4):504-535.

Frenel et al., "Serial Next-Generation Sequencing of Circulating Cell-Free DNA Evaluating Tumor Clone Response to Molecularly Targeted Drug Administration", Clinical Cancer Research, 2015, 21(20):4586-4596.

Paweletz et al., "Bias-Corrected Targeted Next-Generation Sequencing for Rapid, Multiplexed Detection of Actionable Alterations in Cell-Free DNA from Advanced Lung Cancer Patients", 2015, Clinical Cancer Research, 22 (4):915-922.

Plagnol et al., "Analytical validation of a next generation sequencing liquid biopsy assay for high sensitivity broad molecular profiling" PLoS ONE, 2018, 13(3):e0193802.

Strickler et al., "Genomic landscape of cell-free DNA in Patients with colorectal cancer" American Association for Cancer Research, 2018, 8(2):1-24.

Wills et al., "Role of liquid biopsies in colorectal cancer" Current Problems in Cancer, 2018, 42(6):593-600.

Yoneda et al., "A liquid biopsy in primary lung cancer" Surgery Today, 2019, 49:1-14.

Bernabe et al., "What do we need to make circulating tumour DNA (ctDNA) a routine diagnostic test in lung cancer?", European Journal of Cancer, 2017, 81: 66-73.

Jenkins et al., "Plasma ctDNA Analysis for Detection of the EGFR T790M Mutation in Patients with Advanced Non-Small Cell Lung Cancer", Journal of Thoracic Oncology, 2017, 12(7): 1061-1070.

US Food and Drug Administration (FDA), "cobas EGFR Mutation Test v2", Jun. 1, 2016, downloaded from the FDA's website on Oct. 17, 2021.

Thierry et al., "Clinical utility of circulating DNA analysis for rapid detection of actionable mutations to select metastatic colorectal patients for anti-EGFR treatment", Annals of Oncology, 2017, 28: 2149-2159 and Supplemental Figures and Tables.

Dienstmann et al., "Standardized decision support in next generation sequencing reports of somatic cancer variants", Molecular Oncology, 2014, 8: 859-873.

Chen et al., "Circulating Tumor DNA Detection in Early-Stage Non-Small Cell Lung Cancer Patients by Targeted Sequencing", 2016, 6: 31985, p. 1-8.

Arcila, "Molecular Testing of Solid Tumors", 2012, Memorial Sloan Kettering Cancer Center, New York, NY, 2012.

Diaz et al., "Insights into therapeutic resistance from whole-genome analyses of circulating tumor DNA", Oncotarget, 2013, 4(10): 1856-1857.

Xia et al., "Statistical analysis of mutant allele frequency level of circulating cell-free DNA and blood cells in healthy individuals", Scientific Reports, 2017, 7: 7526, p. 1-7.

* cited by examiner

A

B

METHOD OF TREATING A CANCER PATIENT WITHOUT THE NEED FOR A TISSUE BIOPSY

CROSS-REFERENCING

This application is a continuation of U.S. application Ser. No. 16/560,504, filed on Sep. 4, 2019, which claims the benefit of U.S. provisional application Ser. No. 62/727,462, filed on Sep. 5, 2018, which applications are incorporated by reference herein.

BACKGROUND

Non-small cell lung cancer (NSCLC) accounts for over 85% of lung cancer [1], and the majority of patients present with advanced stage disease and are treated with systemic therapies. Great strides have been made in the development of therapies for such patients, including targeted therapies and immunotherapy. Targeted therapies require identification of specific molecular alterations in the cancer [2] and guidelines recommend broad genomic profiling to assess for therapeutic targets. However, the utilization of such comprehensive testing is still limited, often due to inadequate tumor tissue in many patients given the high tissue demands of comprehensive genomic profiling (CGP) testing. A recent review of over 800 patients from routine US community oncology practices revealed that only 59% of patients were profiled for two of the best known genomic alterations (EGFR mutations and ALK fusions), and only 8% received CGP covering all the recommended alterations [3]. Repeat biopsies are costly, often result in patient discomfort, and many patients may experience complications [4]. A recent US Medicare based analysis demonstrated that the average cost of a transthoracic biopsy was $14,587 once treatment of complications was included [5].

Plasma based assays for molecular profiling of tumor mutations through sequencing of cell-free (cfDNA) offer the potential to overcome difficulties associated with tissue based CGP. These less-invasive "liquid biopsies" are now entering routine clinical practice, with recent National Comprehensive Cancer Network (NCCN) guidelines recommending their use in NSCLC patients when tissue biopsy is not available [6].

Cancers that are associated with actionable mutations typically have a better prognosis than other cancers because they can be treated with therapies that specifically target an activity of the protein having the variation. It is common to identify no actionable mutations in cell-free DNA, however. In these cases, it is often unclear whether the tumor itself is not associated with an actionable mutation or the number of molecules that have an actionable mutation in the cfDNA is below the detection limit of the assay. In these cases, a follow-up tissue biopsy is often performed in order to confirm the results obtained from cfDNA.

Follow-up tissue biopsies are expensive, frequently result in patient discomfort, and can cause complications. As such, any methods that allow treatment decisions to be made using data obtained from sequencing cfDNA alone, i.e., without performing a tissue biopsy, have significant value.

SUMMARY

Some embodiments of the present method are based, at least in part, on the discovery of a correlation between the identification of non-actionable sequence variations in cfDNA from a patient and lack of actionable sequence variations in a tissue biopsy from the same patient, if no actionable sequence variations are found in the cfDNA. This correlation may be practically applied to make treatment decisions without having to perform a follow-up biopsy.

Provided herein, among other things, is a method of treating a cancer patient without the need for a tissue biopsy. In some embodiments, the method may comprise (a) performing or having performed a sequencing assay on cell-free DNA (cfDNA) from a sample of blood from the patient to determine if the cell-free DNA comprises actionable and/or non-actionable sequence variations in one or more target genes, and (b) treating the patient using the following method: i. administering a therapy that is targeted to an actionable sequence variation if the patient is identified as having the actionable sequence variation, and ii. administering a non-targeted therapy in the absence of any follow-up genetic testing on DNA extracted from a tissue biopsy if one or more non-actionable sequence variations and no actionable sequence variations are identified.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
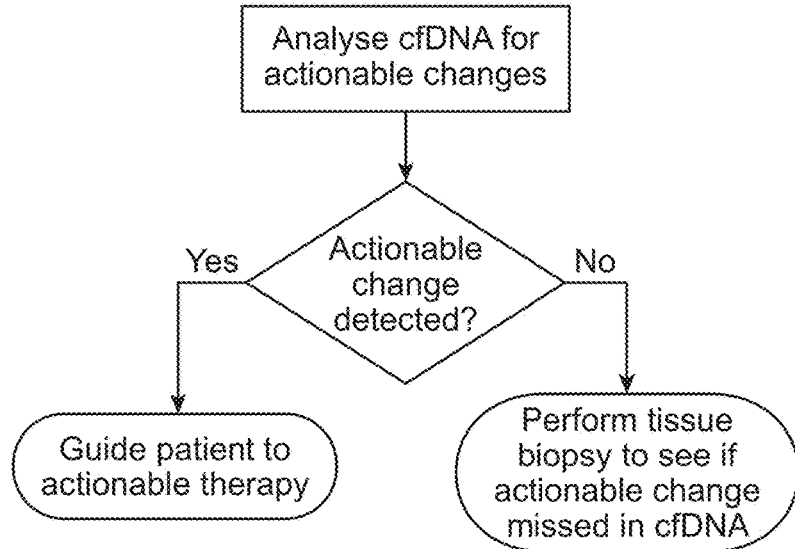
FIG. 1 shows two flow charts A and B. Flow chart A illustrates the standard approach for making treatment decisions, which are based on actionable actionable changes only. Some of the principles of the present "rule out" method are illustrated in flow chart B.
Figure 1:
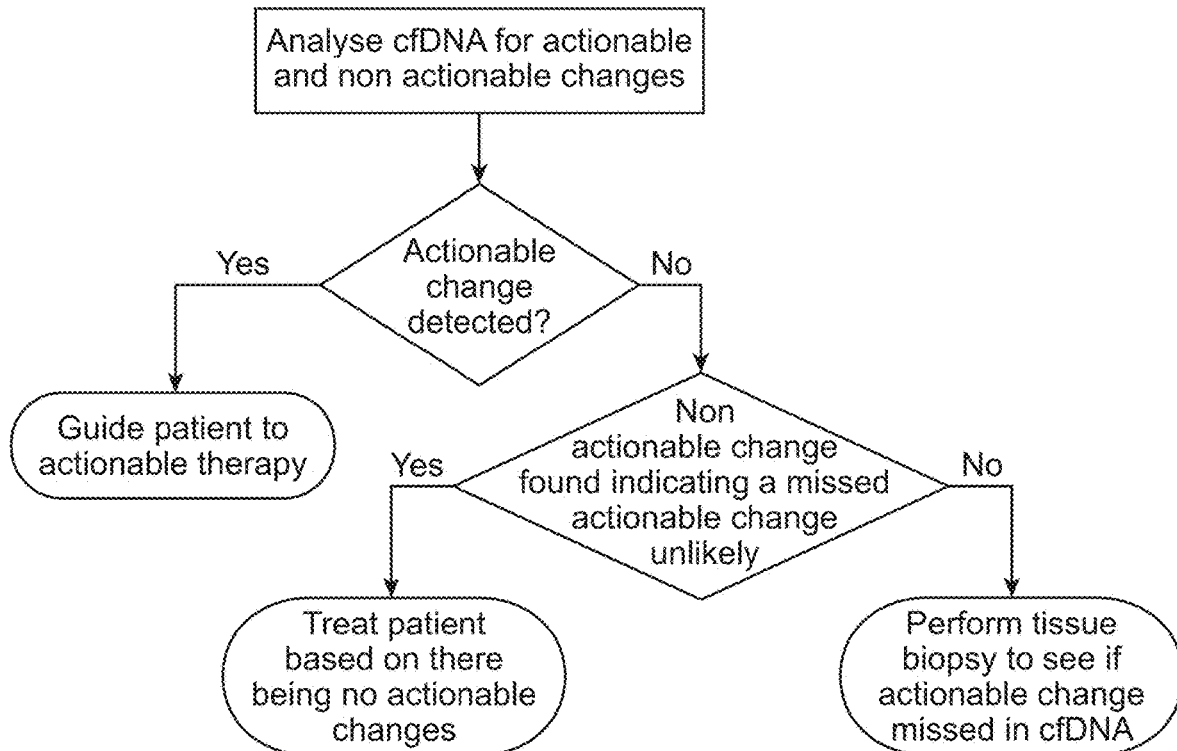

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale &

Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "sequencing at least part of the coding sequences" refers to sequencing at least 20% of, at least 40% of, at least 60% of, at least 80% of, or at least 90% of (e.g., all of), of the coding sequences.

The term "reference sequence", as used herein, refers to a known nucleotide sequence, e.g. a chromosomal region whose sequence is deposited at NCBI's Genbank database or other databases, for example. A reference sequence can be a wild type sequence.

As used herein, the terms "cell-free DNA from the bloodstream" "circulating cell-free DNA" and "cell-free DNA" ("cfDNA") refers to DNA that is circulating in the peripheral blood of a patient. The DNA molecules in cell-free DNA may have a median size that is below 1 kb (e.g., in the range of 50 bp to 500 bp, 80 bp to 400 bp, or 100-1,000 bp), although fragments having a median size outside of this range may be present. Cell-free DNA may contain circulating tumor DNA (ctDNA), i.e., tumor DNA circulating freely in the blood of a cancer patient or circulating fetal DNA (if the subject is a pregnant female). cfDNA can be obtained by centrifuging whole blood to remove all cells, and then isolating the DNA from the remaining plasma or serum. Such methods are well known (see, e.g., Lo et al, Am J Hum Genet 1998; 62:768-75). Circulating cell-free DNA can be double-stranded or single-stranded. This term is intended to encompass free DNA molecules that are circulating in the bloodstream as well as DNA molecules that are present in extra-cellular vesicles (such as exosomes) that are circulating in the bloodstream.

As used herein, the term "circulating tumor DNA" (or "ctDNA") is tumor-derived DNA that is circulating in the peripheral blood of a patient. ctDNA is of tumor origin and originates directly from the tumor or from circulating tumor cells (CTCs), which are viable, intact tumor cells that shed from primary tumors and enter the bloodstream or lymphatic system. The precise mechanism of ctDNA release is unclear, although it is postulated to involve apoptosis and necrosis from dying cells, or active release from viable tumor cells. ctDNA can be highly fragmented and in some cases can have a mean fragment size about 100-250 bp, e.g., 150 to 200 bp long. The amount of ctDNA in a sample of circulating cell-free DNA isolated from a cancer patient varies greatly: typical samples contain less than 10% ctDNA, although many samples have less than 1% ctDNA and some samples have over 10% ctDNA. Molecules of ctDNA can be often identified because they contain tumorigenic mutations.

As used herein, the terms "treat", "treatment" and "treating" or the like herein refers to administering a compound or pharmaceutical composition as provided herein for therapeutic purposes. A treatment involves administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

As used herein, the term "therapeutically effective amount" refers to the amount of a compound that, when administered to a patient having a disease, is sufficient to effect such treatment for the disease. The "therapeutically effective amount" will vary depending on the compound, the disease and its severity and the age, weight, etc., of the subject to be treated.

As used herein, the term "tissue biopsy" refers to a sample of cancerous tissue taken from the body in order to examine it more closely. A biopsy may be from bone marrow, skin or from an internal organ and may be collected by an endoscopic biopsy (e.g., cystoscopy, bronchoscopy or colonoscopy), a fine needle aspiration, a core needle, or surgery for example.

As used herein, the term "actionable sequence variation" is a sequence variation for which there is a therapy that specifically targets the activity of the protein having the variation. In many embodiments an actionable sequence variation causes an increase in an activity of the protein, thereby resulting in cells containing the variation to grow, divide and/or metastasize without check and in combination with other variations, such as in tumour suppressor genes, leading to cancer.

As used herein, the term "therapy that is targeted to an actionable sequence variation" is a therapy that targets the activity of the protein having the sequence variation. Therapy that is targeted to an actionable sequence variation often inhibits an activity of the mutated protein. Examples of actionable sequence variations for non-small cell lung cancer and some other cancers, as well as therapies that target those actionable variations, are listed below.

As used herein, the term "non-actionable sequence variation" is a sequence variation for which there is no therapy that is specifically targeted to the activity of the protein having the variation.

As used herein, the term "non-targeted therapy" is a therapy that is not targeted to a particular sequence variation. Non-targeted therapies include radiation therapy, systemic or local chemotherapy, hormone therapy, immunotherapy (e.g., immune checkpoint inhibition) and surgery. Examples of systemic chemotherapies for non-small cell lung cancer and some other cancers include platinum based doublet chemotherapy such as the combination of cisplatin and pemetrexed and the combination of cisplatin and gemcitabine.

As used herein, the term "mutually exclusive" refers to sequence variations that tend not to occur together in the same patient. Somatic mutations in the pathways that drive cancer development tend to be mutually exclusive across tumors. Such variations are identified through analysis of hundreds of tumor samples. See, for example, Cisowski et al (Small GTPases 2017 8: 187-192) and Mark et al (Bioinformatics 2016 32: i736-i745). For example, KRASG12D and BRAFV600E are mutually exclusive in lung, colorectal and other cancers (see, e.g., Sparks Cancer Res 58: 1130-1134 and Cisowski, supra), although many others are known.

As used herein, the terms "genetic test" and "genetic testing" refer to any assay that is capable of detecting sequence variations (e.g., mutations) in DNA or RNA. A genetic test may be done by sequencing, microarray, multiplex ligation-dependent probe amplification, Invader assay, primer extension, ligation, or PCR such as ARMS-PCR or real time PCR, for example.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Provided herein is a method of treating a cancer patient without the need for a tissue biopsy. In some embodiments, the method may comprise: (a) performing or having performed a sequencing assay on cell-free DNA (cfDNA) from a sample of blood from the patient to determine if the cell-free DNA comprises actionable and/or non-actionable sequence variations in one or more target genes, and (b) treating the patient by i. administering a therapy that is targeted to an actionable sequence variation if the patient is identified as having the actionable sequence variation, and ii. administering a non-targeted therapy in the absence of any follow-up genetic testing on DNA extracted from a tissue biopsy if one or more non-actionable sequence variations and no actionable sequence variations are identified.

For non-small cell lung cancer, actionable variants are most commonly found in EGFR, ALK, ROS1, and BRAF, where the actionable variations in EGFR are activating mutations, the actionable variations in ALK include ALK gene fusions, the actionable variations in ROS1 include ROS1 gene fusions; and the actionable variations in BRAF are activating mutations. Tumors that harbor activating genomic alterations in the corresponding kinase region of genes including EGFR and BRAF that result in constitutive activation and have been identified as driver mutations (see, e.g., Gridelli et al, Nat Rev Dis Prim. 2015, which is incorporated by reference herein). Likewise, chromosomal rearrangements between both ALK and ROS1 and fusion partners, have been identified as drivers. This results from either ALK or ROS1's kinase domain being put under the control of a new promoter. Targeted therapies directed against these activating alterations in EGFR, ALK, ROS1 and BRAF have been approved for use in patients harboring these activating mutations and fusions, and thus, these are described as "actionable" mutations. As such, in some embodiments, the target genes assessed for actionable sequence variations comprise EGFR, ALK, ROS1, and BRAF. For example, in some embodiment the method may further comprise sequencing at least part of the coding sequences of EGFR and BRAF and determining whether there are any rearrangements in ALK and ROS1 that would result in the production of a fusion protein.

Table 1 below shows examples of actionable variations in EGFR, ALK, ROS1 and BRAF as well as therapies that are targeted to cancers, e.g., non-small cell lung cancer, that are associated with those actionable sequence variations. These therapies should not be limited to non-small cell lung cancer because the variations can be found in a variety of different cancer types. Many other actionable sequence variations are known.

TABLE 1

Actionable variations and therapies targeted to those variations

| Gene | Actionable sequence variation | Targeted therapy |
| --- | --- | --- |
| EGFR | L858R, exon 19 deletion, L861Q, G719X, p.S768I, V765A, T783A, V774A, S784P, and L861X | EGFR tyrosine kinase inhibitor (TKI) therapy using e.g., erlotinib (Tarceva), afatinib (Gilotrif), gefitinib (Iressa) or osimertinib (Tagrisso). |
| ALK | EML4-ALK, STRN-ALK, KIF5B-ALK, and TFG-ALK | ALK tyrosine kinase inhibitor (TKI) therapy using, e.g., crizotinib (Xalkori), ceritinib (Zykadia), alectinib (Alecensa) |

TABLE 1-continued

Actionable variations and therapies targeted to those variations

| Gene | Actionable sequence variation | Targeted therapy |
|---|---|---|
| ROS1 | CD74-ROS1, SLC34A2-ROS1, SDC4-ROS1, TPM3-ROS1, and EZR-ROS1 | or brigatinib (Alunbrig). ROS1 tyrosine kinase inhibitor (TKI) therapy using, e.g., crizotinib (Xalkori), entrectinib (RXDX-101), lorlatinib (PF-06463922), crizotinib (Xalkori), entrectinib (RXDX-101), lorlatinib (PF-06463922), ropotrectinib (TPX-0005), DS-6051b, ceritinib, ensartinib or cabozantinib (Cometriq, Cabometyx). |
| BRAF | V600E, L601G, K601E, L597V/Q/R and G469V/S/R/E/A | BRAF inhibitor therapy using, e.g., emurafenib (Zelboraf), dabrafenib (Tafinlar), and encorafenib (Braftovi) or trametinib (Mekinist) |

In some embodiments, the target genes assessed for actionable sequence variations also include MET, RET and HER2. Actionable sequence variations in MET include high-level MET amplification or MET exon 14 skipping mutation, the targeted treatment for which include, TKI therapy, e.g., crizotinib (Xalkori). Actionable sequence variations in RET include RET fusions, including KIF5B-RET, TRIM33-RET, CCDC6-RET, NCO4A-RET fusions, the targeted treatment for which include cabozantinib (Cometriq, Cabometyx) and vandetanib (Caprelsa). Actionable sequence variations in HER2 (ERBB2) include HER2 Exon 20 insertion, the targeted treatment for which include ado-trastuzumab emtansine (Kadcyla). In some embodiments, two or more mutations may be only be clinically actionable when present together.

BRAF is the human gene that encodes a protein called B-Raf. The gene is also referred to as proto-oncogene B-Raf and v-Raf murine sarcoma viral oncogene homolog B, while the protein is more formally known as serine/threonine-protein kinase B-Raf. The BRAF gene is located on chromosome 7q34, and covers approximately 190 kb. It contains at least 19 exons and encodes a full-length transcript of 2,510 bp (NM_00433). At least seven variant transcripts have been identified, which are products of alternative splicing. From these various transcripts, several proteins are translated, including the full-length, 94-95 kD, 783 amino acid product. See, e.g., Sithanandam et al, Oncogene 1990 5: 1775-80; and Meyer et al Journal of Carcinogenesis 2003 2, 7. The sequence of human BRAF and its structure are set forth in entry 673 in NCBI's gene database; NCBI Reference Sequence: NG_007873.3.

EGFR encodes a transmembrane glycoprotein that is a member of the protein kinase superfamily. The gene maps to 7p11.2. The EGFR gene contains 28 exons and spans nearly 200 kb. Intron 1 spans 123 kb. The gene contains several repeat elements, including SINEs and LINEs, as well as a trinucleotide (TGG/A) repeat-rich region in intron 15, and 2 long CA repeats in intron 27. The sequence of the human EGFR gene and its structure are set forth in entry 1956 in NCBI's gene database; NCBI Reference Sequence: NG_007726.3. See, e.g., Zhang et al J Med Genet. 2007 44: 166-72.

ALK encodes a receptor tyrosine kinase, which belongs to the insulin receptor superfamily. ALK is situated on the short arm of chromosome 2 (2p23.2). The gene contains over 30 distinct introns and transcription produces about 8 different mRNAs, with several alternatively spliced variants and unspliced forms. The sequence of the human ALK gene and its structure are set forth in entry 427 in NCBI's gene database; NCBI Reference Sequence: NC_000002.12. See, e.g., Figueiredo-Pontes et al J Thorac Oncol. 2014 February; 9(2): 248-253.

ROS1 encodes a receptor tyrosine kinase with structural similarity to the ALK protein; it is encoded by the c-ros oncogene, which is found on Chromosome 6 in the human genome. Approximately 2% of lung tumors harbor ROS1 fusions (Bergethon et al. 2012. J Clin Oncol. 2012 Mar. 10; 30(8):863-70). The sequence of the human ROS1 gene and its structure are set forth in entry 6098 in NCBI's gene database; NCBI Reference Sequence: NG_033929.1. See, e.g., Uguen et al Future Oncol. 2016 12:1911-28.

The target genes assessed for non-actionable sequence variations include any cancer-related gene, including but not limited to AKT1, ALK, BRAF, CCND1, CDKN2A, CTNNB1, EGFR, ERBB2, ESR1, FGFR1, FGFR2, FGFR3, GATA3, GNA11, GNAQ, GNAS, HRAS, IDH1, IDH2, KIT, KRAS, MAP2K1, MET, MYC, NFE2L2, NRAS, NTRK1, NTRK3, PDGFRA, PIK3CA, PPP2R1A, PTEN, ROS1, STK11, TP53 and U2AF1.

In some embodiments, the target genes assessed for non-actionable sequence variations include STK11 and KRAS. The non-actionable sequence variations in STK11 include all single nucleotide variations and indels that result in a coding sequence or splice-site mutation. In some embodiments, a non-actionable sequence variation in STK11 may reduce or abolish the activity of STK11. The non-actionable sequence variations in KRAS include all single nucleotide variations and indels that result in a coding sequence or splice-site mutation and/or one or a combination of hotspot variations selected from the group consisting of G12A, G12C, G12D, G12F, G12I, G12R, G12S, G12V, G13C, G13D, G13R, GQ60-61GK, Q61H, Q61L and Q61R. In some embodiments a non-actionable sequence variation in KRAS may activate KRAS.

In some embodiments, a non-actionable sequence variation may be mutually exclusive to an actionable sequence variation. For example, if a G12D (or other) variation in KRAS is identified, the cancer is unlikely to be associated with an actionable sequence variation. Likewise, in the present study, it was found that non-actionable sequence mutations in STK11 and KRAS are mutually exclusive with actionable sequence variations in EGFR, ALK, ROS1 and BRAF. As such, if a non-actionable mutation in KRAS or STK11 is identified, then the patient may be treated with a non-targeted therapy such as radiation therapy, systemic or local chemotherapy, immunotherapy (e.g., immune checkpoint inhibition) or surgery, without a targeted therapy. For non-small cell lung cancer, if no actionable sequence variations are identified but a non-actionable mutation is found in KRAS or STK11, for example, then the patient may be subjected to chemotherapy using a platinum-based antineoplastic drug such as cisplatin, which may be used on its own or as a combination therapy with pemetrexed or gemcitabine.

In some embodiments, the allele frequency of any non-actionable sequence variation identified in (a) is used to predict the probability of detecting or missing an actionable variant in the same sample. In sequencing a PCR product that contains a sequence variation that is present in a minority of the molecules, some of the sequence reads will be from the variant molecules while others will not (e.g., will be from the "wild type" sequence). The "allele frequency", i.e., frequency of reads that are from the variant molecules can be calculated by, for example, dividing the number of reads from the variant molecules by the total number of reads.

In these embodiments, the method may comprise predicting whether an actionable variant has been missed in a test sample, where the predicting is based on the allele frequency of any non-actionable sequence variation identified and the distribution of allele frequencies in actionable and non-actionable genes in reference samples and, optionally, the calculated sensitivity of the sequencing assay at different allele frequencies. In other words, whether an actionable mutation has been missed in the cfDNA can be determined by examining the distribution of allele frequencies of sequence variations, actionable and non-actionable, in a training set of reference samples with known mutation profiles. In these embodiments, the prediction process may comprise: i) comparing the distribution of allele frequencies of each actionable sequence variation, gene containing multiple variants or group of genes containing multiple variants to each non-actionable variant, gene containing non-actionable variants or group of genes containing non-actionable sequence variations either in tumour material from reference patients with the same cancer or previous cfDNA tests from patients with the same cancer, ii) comparing the allele frequency of the non-actionable variant detected in the test sample to (i) in order to predict the likely allele frequency or distribution of possible allele frequencies of any actionable variants if present; and iii) comparing the likely allele frequency or distribution of possible allele frequencies of actionable variants if present to the sensitivity of the assay at different levels in order to predict if an actionable variant is either not present or could be present but missed. In these embodiments, the distributions of allele frequencies in actionable and non-actionable genes may be compared using a linear regression model.

In some embodiments, the method may comprise analyzing white blood cell DNA from the patient and determining whether any of the actionable or non-actionable sequence variations identified in step (a) are due to hematopoiesis of indeterminate potential or a germ-line variation and can be eliminated from step (b). In these embodiments, the method may involve comparing the genetic variations called using cfDNA to the genetic variations called using the white blood cell DNA. If a variation is identified in both samples, then it may be identified as being more likely to be a germ line variation or a somatic change in hematopoietic stem cells or other blood cells as opposed to a somatic mutation in ctDNA. This embodiment provides a way to identify variations that may be potentially due to clonal hematopoiesis of indeterminate potential (CHIP) (see, generally, Funari et al, Blood 2016 128:3176 and Heuser et al, Dtsch Arztebl Int. 2016 113: 317-322), or may be germ line variants for example.

An alternative embodiment may be used for the treatment of colorectal cancer patient without the need for a tissue biopsy. In this embodiment, the method may comprise: (a) performing or having performed a sequencing assay on cell-free DNA (cfDNA) from a sample of blood from the patient to determine if the cell-free DNA comprises i. one or more RAS mutations in either NRAS or KRAS and ii. non-actionable sequence variations in one or more target genes, and (b) treating the patient using the following method: i. administering a therapy suitable for the treatment of colorectal cancer that contains RAS mutations if the patient is identified as having a RAS sequence variation (e.g., FOLFIRI, FOLFOX or CAPEOX±bevacizumab), and ii. administering an anti-epidermal growth factor receptor (EGFR) therapy (e.g., a therapy that comprises an anti-EGFR therapy such as cetuximab or panitumumab)±chemotherapy (e.g., FOLFIRI or FOLFOX) to the patient in the absence of any follow-up genetic testing on DNA extracted from a tissue biopsy if one or more non-actionable sequence variations and no RAS mutations are identified. In colorectal cancer KRAS is mutated in approximately 40% of cases mostly in exon 2 codons 12 (70-80%) and 13 (15-20%). The remaining mutations are mainly located in exon 3 codons 59-61 and in exon 4, which includes codons 117 and 146. Mutations in NRAS are present in approximately 3% to 5% of colorectal cancer samples particularly in exon 3 codon 61 (60%) and in exon 2 codons 12, 13. In these embodiments, the target genes assessed for non-actionable sequence variations may comprise APC and TP53. Like for the prior embodiments, the allele frequency of any non-actionable sequence variation identified in (a) can be used to predict the probability of detecting or missing a RAS mutation in the sample. In some embodiments the BRAF gene may also be analysed and in the absence of a BRAF V600E mutation being detected any non-actionable sequence variations identified may be used to determine the likelihood of one being missed as patients with such mutations are also unlikely to respond to anti-epidermal growth factor receptor (EGFR) therapy.

In some embodiments, the method may comprise predicting whether a RAS mutation has been missed in a test sample, wherein the predicting is based on the distribution of allele frequencies for the one or more RAS mutations and non-actionable variants in reference samples and, optionally, the calculated sensitivity of the sequencing assay at different allele frequencies. In these embodiments, the predicting may comprise i) comparing the distribution of allele frequencies of each RAS mutation to each non-actionable variant, gene containing non-actionable variants or group of genes containing non-actionable sequence variations either in tumour material from reference patients with the same cancer or previous cfDNA tests from patients with the same cancer, ii) comparing the allele frequency of the non-actionable variant detected in the test sample to (i) in order to predict the likely allele frequency or distribution of possible allele frequencies of the one or more RAS mutations, if present; and iii) comparing the likely allele frequency or distribution of possible allele frequencies of the one or more RAS mutations, if present, to the sensitivity of the assay at different levels in order to predict if a RAS mutation is either not present or could be present but missed. In any embodiment, the distributions of allele frequencies in the one or more RAS mutations and non-actionable variants can be compared using a linear regression model.

This alternative method may also involve analyzing white blood cell DNA from the patient and determining whether any of the RAS mutations or non-actionable sequence variations identified in step (a) are due to hematopoiesis of indeterminate potential or a germ-line variation and can be eliminated from step (b).

Exemplary implementations of the methods described above are schematically illustrated in the flow charts shown in FIGS. 1-4.

Figure 2:
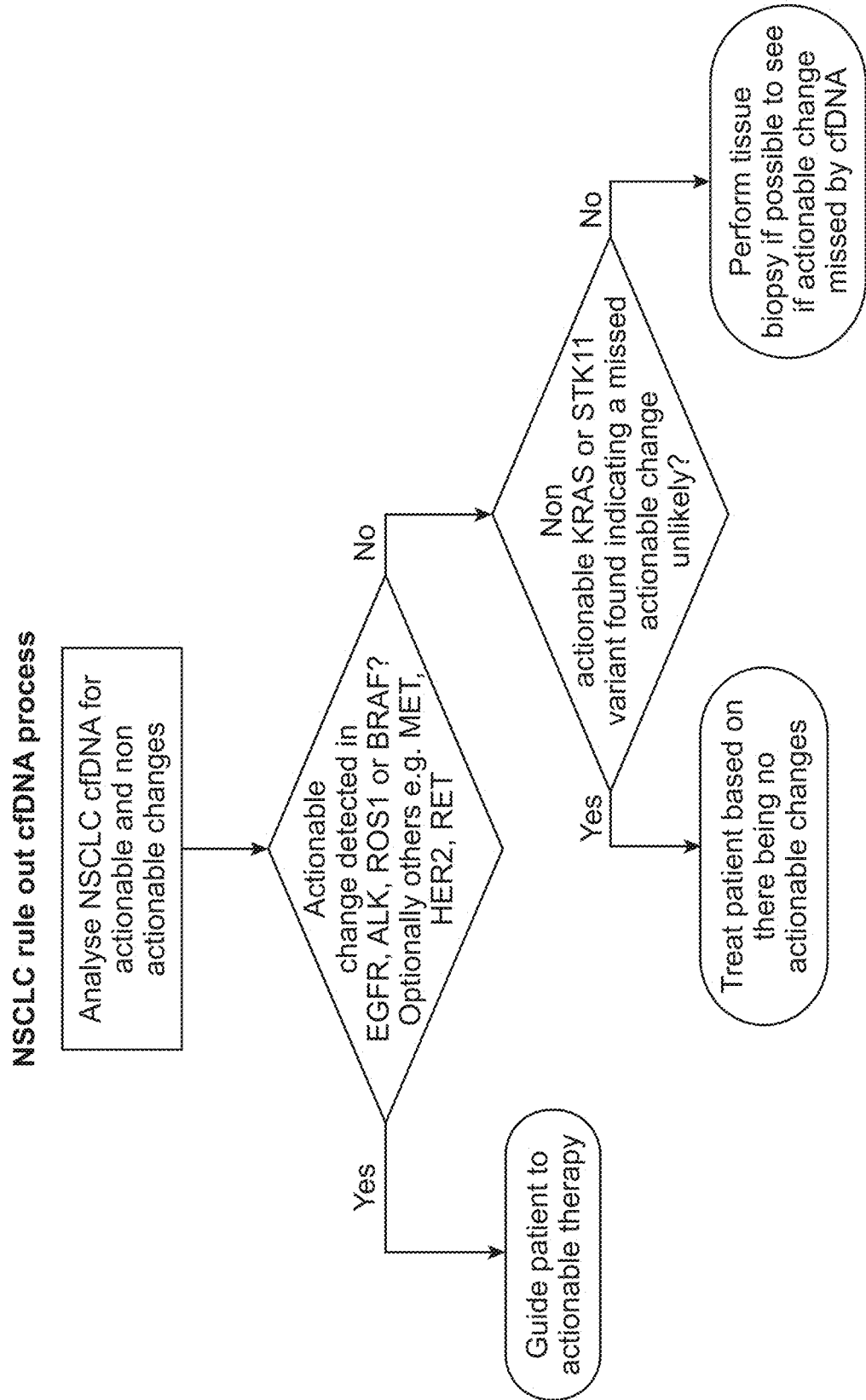
FIG. 2 is a flow chart illustrating how the present method can be used to avoid tissue biopsies in the treatment of non-small cell lung cancer.

FIG. 1, flowchart A, illustrates the conventional way for making treatment decisions using cfDNA. In the conventional method, if no actionable changes are detected in cfDNA, then a tissue biopsy will be obtained and analyzed. FIG. 2, flowchart B, illustrates some of the principles of the present method. In these embodiments, if no actionable changes are detected in cfDNA, then the non-actionable changes in the cfDNA can be examined to determine if an actionable change was missed. If analysis of the non-actionable changes indicates that actionable changes are unlikely, then the patient can be treated in the absence of a tissue biopsy from the patient.

FIG. 2 illustrates one way in which the method of flowchart A of FIG. 1 can be applied to make treatment decision for non-small cell lung cancer (NSCLC). In this method, if there are no actionable changes in EGFR, ALK, ROS1 and BRAF, but there are non-actionable changes in KRAS or STK11, then the patient can be treated in the absence of a tissue biopsy from the patient.

Figure 3:
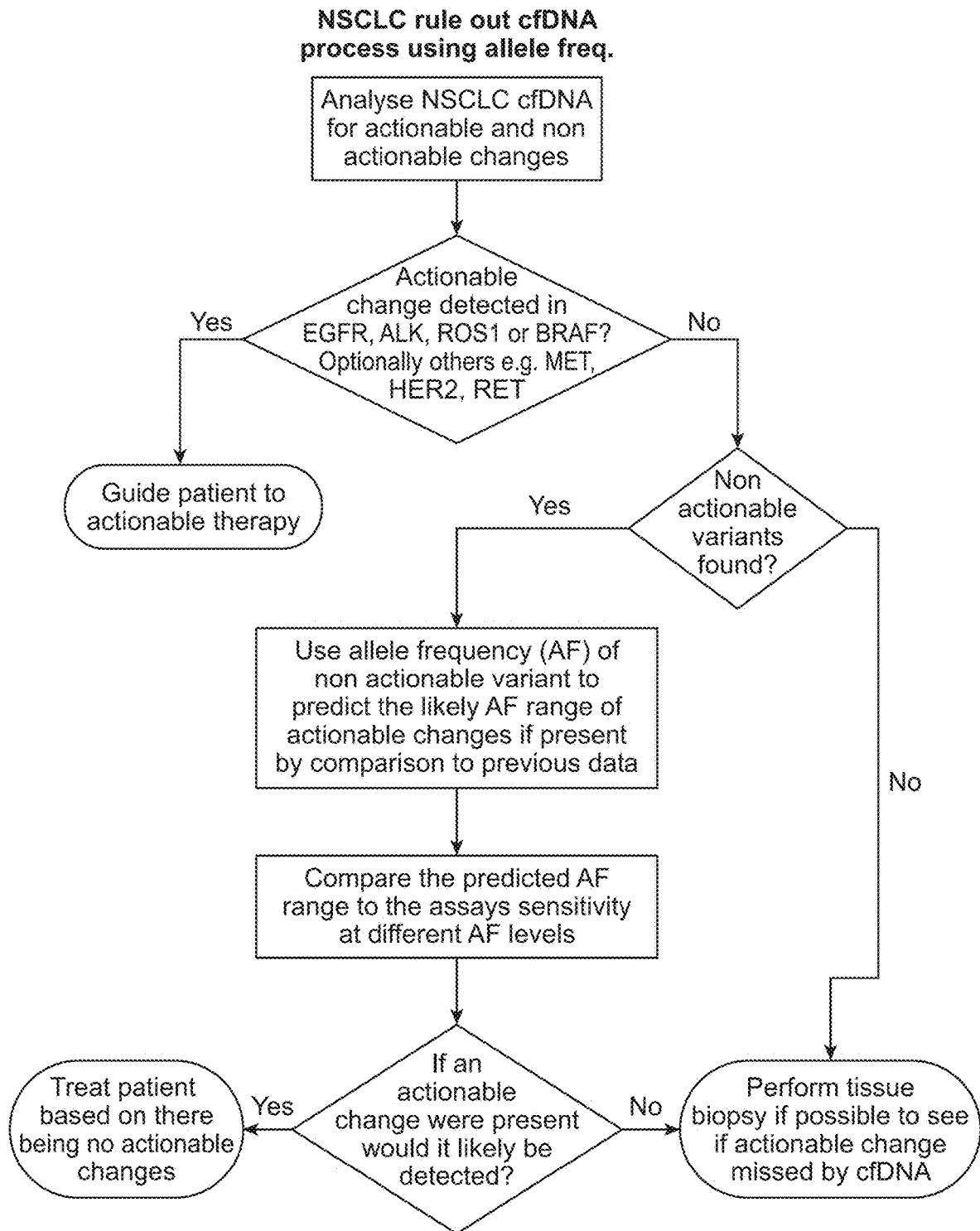
FIG. 3 is a flow chart illustrating a second embodiment of the present method that can be used to avoid tissue biopsies in the treatment of non-small cell lung cancer. This embodiment uses the allele frequency of non-actionable changes to determine the probability that actionable changes could have been missed.

FIG. 3 illustrates one way in which treatment decisions can be made using allele frequencies. In this method, if there are no actionable changes in EGFR, ALK, ROS1 and BRAF, the allele frequency of non-actionable changes can be used to determine the likelihood of whether an actionable change in those genes has been missed.

Figure 4:
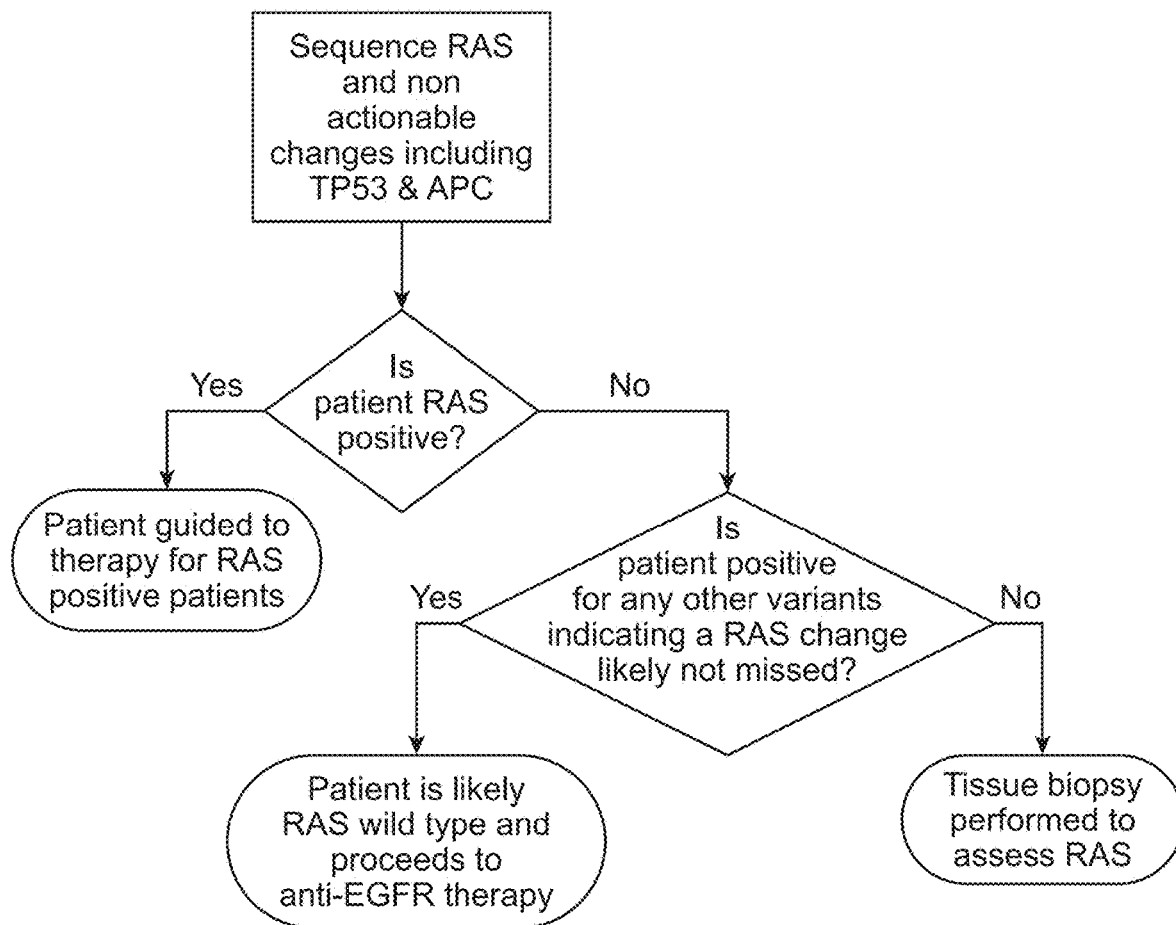
FIG. 4 is a flow chart illustrating how the present approach could be used to make treatment decisions for colorectal cancer patients.

FIG. 4 illustrates one way in which treatment decisions can be made in colorectal cancer (CRC). By analysing non-actionable changes in genes including TP53 and APC, one can predict which patients are unlikely to have a RAS variant and which patients have too little ctDNA to determine if a RAS variant is present and therefore need further tissue testing.

In many embodiments, the method may comprise sequencing at least part of the coding sequences of several genes (e.g., EGFR, BRAF, KRAS and STK11) as well as at least part of ALK and ROS1 in a sample of the cfDNA. Methods for sequencing target sequences in cfDNA are known and, in some embodiments, the method may comprise enriching for or amplifying target sequences by PCR prior to sequencing (see, e.g., Forshew et al, Sci. Transl. Med. 2012 4:136ra68, Gale et al, PLoS One 2018 13:e0194630 and Weaver et al, Nat. Genet. 2014 46:837-843, among many others). ALK and ROS1 fusions may be identified using similar methods, e.g., using PCR and the sequencing the products. These method may make use of primer pairs in which one primer hybridizes to the ALK or ROS1 gene and another primer hybridizes to a gene encoding a potential fusion partner for ALK or ROS1. In some embodiments, the method does not involve shotgun sequencing an unenriched/unamplified sample, or sequencing the entire exome. Rather, the sequencing may be done as part of a larger sequencing effort that targets at least part of the coding sequences for up to 500, e.g., up to 100 or up to 50 genes, focusing on the coding sequences and fusions of the genes of interest. In some embodiments this targeting may be performed by hybrid capture.

After the sequences have undergone initial processing, the sequences are analyzed to identify sequence variations. This may be done by comparing the test sequence to a reference sequence, for each sequence being analyzed, and the identifying positions that contain a change in a nucleotide. In some cases, this may comprise calling mutations de novo (e.g., using the method described by Forshew, supra, or another suitable method) and then determining which of those mutations are actionable or non-actionable. Calling sequence variations in cell-free DNA can be challenging because the variant sequences are generally in the minority (e.g., less than 10% of the sequence). As such, if an amplicon sequencing strategy is employed, the method may comprise: (a) for each nucleotide position of a particular amplicon, determining, e.g., plotting, an error distribution that shows how often amplification and/or sequencing errors occur at different sequencing depths; (b) based on the distribution for each position of the sequence, determining a threshold frequency for each different sequencing depth at or above which a true genetic variation can be detected; (c) sequencing the sample to obtain plurality of reads for an amplicon; and determining, for each position of the amplicon, whether the frequency of a potential sequence variation in the sequence reads is above or below the threshold. Mutation may be identified (or "called") at a position if the frequency of sequence reads that contain the variation is above the threshold. In some cases, a substitution may be identified only if it occurs in the same amplicon from multiple independent amplification reactions. As would be apparent, if the sequencing is done using an amplicon approach, the method may comprise amplifying the coding sequences of the genes in a multiplex PCR reaction in which at least 10 amplicons (e.g., more than 10 and less than 50,000 amplicons, more than 10 and less than 10,000, more than 10 and less than 5,000 amplicons, more than 10 and less than 1,000 amplicons or more than 10 and less than 500 amplicons) or more than 10 and less than 100 amplicons are amplified (in duplicate, triplicate or quadruplicate, for example) and sequencing the amplicons. More or less amplicons can also be sequenced, if needed. In some embodiments, the primers used for amplification may not be completely specific for a single sequence, which can allow several hundred or several thousand amplicons to be consistently amplified in a single reaction. The amplicons sequenced can be of any suitable length and may vary in length. In some embodiments, the length of each amplicon, independently, may be in the range of 50 bp to 500 bp, although longer or shorter amplicons may be used in some implementations.

Next, the sequence variations are identified, the sequence variations may be classified as actionable or non-actionable. In some embodiments, the method may further comprise sequencing at least part of the coding sequences of KRAS and STK11 in the sample of cfDNA. In these embodiments, the method may involve analyzing the sequences to determine if there are any activating mutations in KRAS and loss of function mutations in STK11. Examples of loss of function mutations include, but are not limited to mutations that generate a stop codon, mutations at splice junctions, and mutations that substitute a critical amino acid for another.

A patient that, based on the analysis of the patient's cell-free DNA, appears to be have no actionable mutations in EGFR, ALK, ROS1 or BRAF but a non-actionable mutation in KRAS or STK11 can be treated with a non-targeted therapy without a tissue biopsy.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform, QIAGEN's GeneReader platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. Nanopore sequencing could be employed in certain cases.

In some embodiments, the method may comprise providing a report indicating whether there are any: i. actionable sequence variations, e.g., in EGFR, ALK, ROS or BRAF and ii. non-actionable sequence variations, e.g., in KRAS or STK11. In addition, a report may provide options for approved (e.g., FDA approved) therapies if an actionable sequence variation is identified (e.g., a list of targeted therapies). If no actionable sequence variations and one or more non-actionable sequence variations are identified, then the report may: i. provide options for approved (e.g., FDA approved) non-targeted therapies for the cancer and ii. a statement that indicates that analysis of a tissue biopsy is unnecessary before treatment. In some embodiments the report may provide levels of confidence that specific actionable variants are not present.

In some embodiments, the report may be in an electronic form, and the method comprises forwarding the report to a remote location, e.g., to a doctor or other medical professional to help identify a suitable course of action, e.g., to identify a suitable therapy for the subject. The report may be used along with other metrics to determine whether the subject may be susceptible to immune checkpoint inhibition.

In any embodiment, a report can be forwarded to a "remote location", where "remote location," means a location other than the location at which the sequences are analyzed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet, including email transmissions and information recorded on websites and the like. In certain embodiments, the report may be analyzed by an MD or other qualified medical professional, and a report based on the results of the analysis of the sequences may be forwarded to the patient from which the sample was obtained.

In computer-related embodiments, a system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for providing a score using the measurements described above as inputs. The computer processor is coupled to the storage component and configured to execute the instructions stored in the storage component in order to receive patient data and analyze patient data according to one or more algorithms. The display component may display information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

EXAMPLES

Aspects of the present teachings can be further understood in light of the following examples, which should not be construed as limiting the scope of the present teachings in any way.

Methods

Patients with advanced non-squamous NSCLC were recruited in 2 prospective US clinical studies (INI-001 [NCT02906852], GRN-ALV [NCT03116633]). Samples from 10 patients were also obtained from a commercial biobank [Asterand, US].

Patients were included if they met the following criteria: written informed consent; aged 18, stage IIIB/IV NSCLC, had not received therapy for advanced NSCLC; blood for plasma ctDNA analysis collected within 12 weeks of NSCLC tissue biopsy; no anti-cancer therapy between the tissue and plasma collection.

The primary aim was to examine concordance of ctDNA and tissue profiling. All patients meeting the above criteria were eligible regardless of tissue availability to allow the comparison of ctDNA profiles in patients with and without tissue for profiling.

All studies were undertaken within recognized ethical principles laid down in ICH GCP and the declaration of Helsinki and were subject to IRB/Ethical review and approval.

ctDNA, tissue analysis and concordance analysis: Blood was collected into Streck-DNA tubes (Streck Inc, US) and shipped to the Inivata CLIA accredited laboratory (Morrisville, US) for InVision ctDNA analysis. Full assay details have been described previously [9, 10]. Briefly, blood was processed to plasma by centrifugation. Following plasma extraction, plasma was stored at −80° C. according to validated specifications until analysis in batch. Cell free DNA (cfDNA) was extracted using the QIAamp Circulating Nucleic Acid kit (Qiagen). Following quality control, sequencing libraries were prepared using a two-step amplification process, and libraries were sequenced by Illumina NextSeq 500. Sequencing data were analyzed using the Inivata analytical pipeline to identify genomic alterations.

Where sufficient tissue was available, CGP was performed in a CLIA-certified laboratory (Caris Life Science, US). Direct sequence analysis was performed on genomic DNA isolated from formalin-fixed paraffin-embedded (FFPE) tumor samples using the Illumina NextSeq platform. An Agilent custom-designed SureSelect XT assay was used to enrich 592 whole-gene targets and all variants reported were detected with >99% confidence. Fusion analysis was performed using the Archer FusionPlex Solid Tumor Panel and the Illumina MiSeq. When patients had insufficient tissue for CGP, tissue testing was allowed as per the treating institutions routine pathways. Where both central CGP and local data was available, the centralized CGP data was utilized for concordance analysis.

Both InVisionFirst and tissue analysis were performed blinded from each other. Calls made in either ctDNA or tissue in genomic regions that were not covered by testing in the other were excluded from concordance analysis. The calling nomenclature for all identified mutations was reviewed along with underlying sequencing data where present to ensure that mutations were named consistently and all calls were correctly classified for concordance.

ddPCR validation data: Thirty-three patients from the INI-001 study also underwent plasma ddPCR testing for key genomic alterations (KRAS G12C/G12D/G12V, EGFR exon19del/T790M/L858R, BRAF V600E, ALK/ROS1 fusions) via a commercial assay provider (GeneStrat, Biodesix Inc, US) as part of their routine standard of care. Blood samples were collected and shipped according to the standard specifications. Analysis was completed without any knowledge of tissue or ctDNA testing results.

Statistical analysis: All analyses were performed using R version 3.2.5. In the concordance analysis, the data was summarized using a 2 by 2 table, referring to tissue as the standard:

|  | Tissue positive | Tissue negative |
|---|---|---|
| Plasma positive | True positive (TP) | False positive (FP) |
| Plasma negative | False negative (FN) | True Negative (TN) |

The following definitions were used:
Sensitivity=TP/(TP+FN)
Specificity=TN/(TN+FP)
PPV=TP/(TP+FP)
NPV=TN/(TN+FN)

Results

Figure 5:
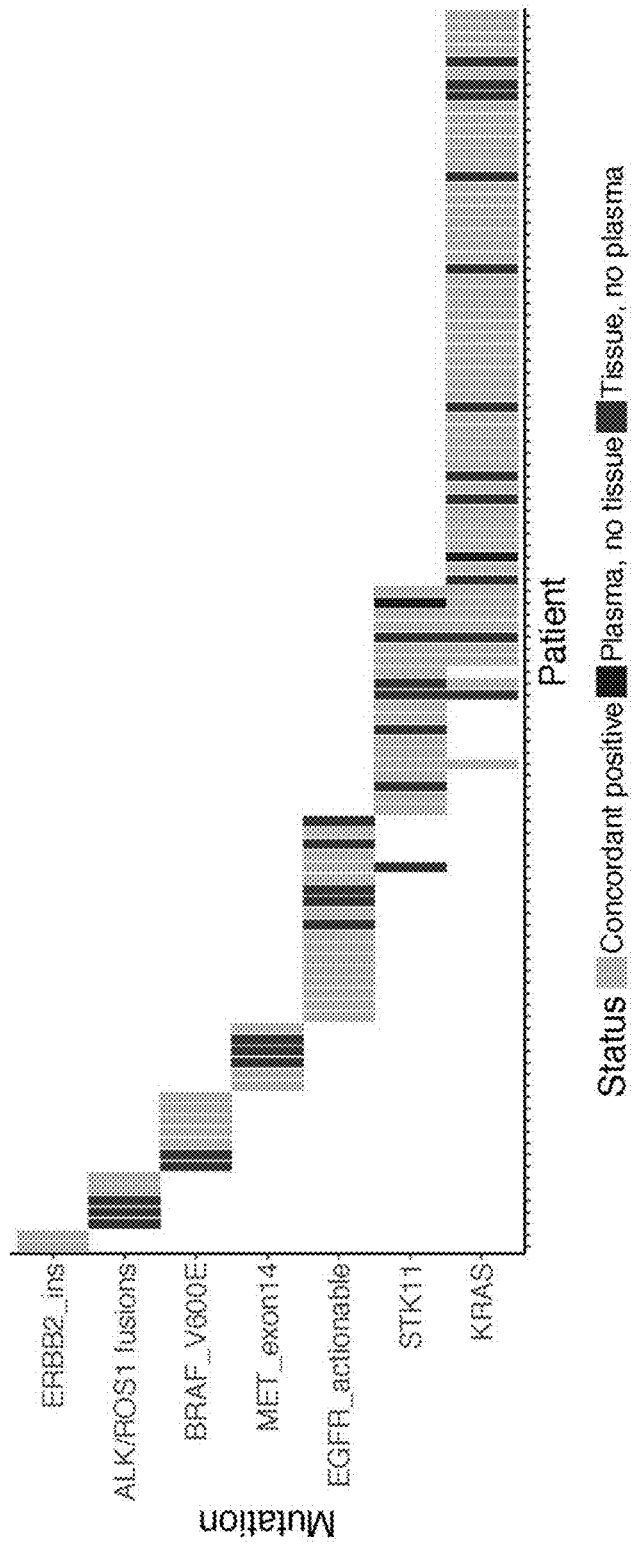
FIG. 5 shows concordance data for clinically relevant alterations detected in the 8 key genes (ERBB2, ALK, ROS1, BRAF, MET, EGFR, STK11 and KRAS) when both tissue and ctDNA testing was successful.

A total of 264 eligible patients were recruited across 41 centers. Baseline demographics for the cohort are shown in Table 2 and were consistent with expectations. Patients with and without tissue testing had similar demographics. A summary of some of the results is shown in FIG. 5.

TABLE 2

Cohort Demographics

|  | Patients without tissue for testing | Patients with tissue for testing | All patients |
|---|---|---|---|
| n | 86 | 178 | 264 |
| Age (mean (sd)) | 68.2 (10.9) | 66.6 (11.1) | 67.1 (11.0) |
| Smoking status (%) |  |  |  |
| Current smoker | 22.1 | 31.5 | 28.4 |
| Former smoker | 60.5 | 55.1 | 56.8 |
| Never smoked | 17.4 | 12.9 | 14.4 |
| Missing | 0.0 | 0.6 | 0.4 |
| Race (%) |  |  |  |
| American indian or Alaska native | 0.0 | 0.6 | 0.4 |
| Asian | 3.5 | 1.7 | 2.3 |
| Black or African American | 7.0 | 11.2 | 9.8 |
| White | 84.9 | 86.0 | 85.6 |
| Other | 4.7 | 0.6 | 1.9 |
| Histology (%) |  |  |  |
| Adenocarcinoma | 94.2 | 96.1 | 95.5 |
| Large cell carcinoma | 1.2 | 0.0 | 0.4 |
| Neuroendocrine carcinoma | 0.0 | 0.6 | 0.4 |
| Sarcomatoid | 1.2 | 0.0 | 0.4 |
| Missing | 3.5 | 3.4 | 3.4 |
| BMI (mean (sd)) | 27.1 (6.0) | 26.4 (6.1) | 26.6 (6.1) |
| Sex = M (%) | 51.2 | 47.2 | 48.5 |
| Cancer stage (%) |  |  |  |
| 3B | 10.5 | 16.9 | 14.8 |
| 4 | 88.4 | 79.2 | 82.2 |
| Missing* | 1.2 | 3.9 | 3.0 |

*All patients included were confirmed as eligible based on TNM staging

InVisionFirst ctDNA Profile

All patients were successfully tested for SNVs, indels and amplifications. Testing for ALK/ROS1 fusions was successful in 252 patients (95.5% of patients). Overall, 204 (77.3%) patients had one or more alterations detected by ctDNA. The mean number of alterations identified per patient was 1.5. Of the SNVs and indels identified, 35.5% had an allele fraction lower than 1%, and 23.1% had an allele fraction lower than 0.5%.

The predominant alterations identified were TP53 (47% patients) and KRAS (32% patients). Twenty-seven SNVs or indels in EGFR exon 18-21 were identified in 26 patients (10%). Gene fusions were identified in 5 patients (2%), including EML4-ALK in 4 patients and CD74-ROS1 in 1 patient. The pattern and frequency of genomic alterations was similar across patients with and without tissue.

Tissue Testing and Tissue-ctDNA Concordance

Of the 264 recruited patients, 178 had successful tissue testing for at least 1 genomic alteration. One hundred and sixty five patients (62.5%) were tested for any point mutation/indel, and 159 (60.2%), were tested for ROS1 and/or ALK fusions. The most frequently tested gene in tissue was EGFR (164 patients, 62.1%). A total of 95 patients were tested for all 8 of the key genes (ERBB2, ALK, ROS1, BRAF, MET, EGFR, STK11 and KRAS), and 121 were tested for fusions in ALK and ROS1 and mutations in EGFR, MET and BRAF.

Considering tissue as the reference, the sensitivity of InVisionFirst across the entire panel was 70.6%. Considering only clinically actionable alterations in 8 genes of most relevance, the sensitivity was 73.9% with a PPV of 97.8% (Table 3). The PPV was 100% when only considering the directly actionable variants (ALK/ROS1 fusions/EGFR exons18-21/ERBB2 insertions/MET exon14 splice/BRAF V600E).

TABLE 3

Summary of tissue concordance data.

| | Tissue and Plasma | Tissue only | Plasma only | No call | PPV | NPV | Sensitivity | Specificity |
|---|---|---|---|---|---|---|---|---|
| ALK/ROS1 fusions | 2 | 3 | 0 | 292 | 100.0 | 99.0 | 40.0 | 100.0 |
| BRAF V600E | 5 | 2 | 0 | 140 | 100.0 | 98.6 | 71.4 | 100.0 |
| EGFR (exons 18-21) | 13 | 5 | 0 | 146 | 100.0 | 96.7 | 72.2 | 100.0 |
| ERBB2 exon 20 ins | 2 | 0 | 0 | 137 | 100.0 | 100.0 | 100.0 | 100.0 |
| KRAS | 48 | 12 | 1 | 86 | 98.0 | 87.8 | 80.0 | 98.9 |
| MET exon 14 splice | 3 | 3 | 0 | 133 | 100.0 | 97.8 | 50.0 | 100.0 |
| STK11 | 15 | 6 | 1 | 93 | 93.8 | 93.9 | 71.4 | 98.9 |
| Key 8 genes* | 88 | 31 | 2 | 1027 | 97.8 | 97.1 | 73.9 | 99.8 |
| All Genes | 156 | 65 | 32 | 4135 | 83.0 | 98.5 | 70.6 | 99.2 |

*Key 8 genes refers to the combination of all directly actionable mutations (ALK/ROS1 fusions, BRAF V600E, EGFR exons 18-21, ERBB2 insertions, MET exon 14 splice) and KRAS and STK11 variants.

InVisionFirst detected 32 mutations in 23 patients that were not detected by tissue analysis, including TP53 (17 mutations), PIK3CA (3), NRAS (3) and ERBB2 (2). For 30 of these, read alignment data from tissue NGS was available. Review by the testing laboratory found evidence of the mutations below the standard calling threshold in 6 of the 30 mutations: PIK3CA E542K (3 occurrences), KRAS G12C, MET D1249N, and TP53 V197M.

Two hundred and four patients (77.27%) had at least one mutation detected by InVisionFirst. In this cohort, the sensitivity was 88.0% for clinically relevant alterations in the key 8 genes.

Utility Analysis

Tissue CGP was performed for all patients where sufficient tissue was available and was funded as part of the study. The tissue testing undertaken across the study is therefore considered representative of the real-world potential utility of tissue testing within this population. Despite this, InVisionFirst testing resulted in a much higher rate of testing compared to tissue testing across the entire recruited population. Table 4 details the most clinically relevant alterations detected across all patients enrolled. A total of 48 patients qualified for a targeted treatment based on InVisionFirst testing, and 38 patients based on tissue testing. 48% of the actionable alterations detected by InVisionFirst were in patients who had not been tested for that alteration in tissue due to incomplete tissue testing despite funding by the study.

TABLE 4

Summary of actionable and rule-out status using the liquid biopsy data.

| Class | Subclass | Plasma (n) | Plasma (%) | Tissue (n) | Tissue (%) |
|---|---|---|---|---|---|
| Total | | 264 | 100.00 | 264 | 100.00 |
| Actionable | | 48 | 18.18 | 38 | 14.39 |
| | EGFR exons 18-21 | 26 | 9.85 | 18 | 6.82 |
| | ALK-ROS1 fusions | 5 | 1.89 | 5 | 1.89 |
| | ERBB2 exon 20 insertions | 4 | 1.52 | 2 | 0.76 |
| | BRAF V600E | 6 | 2.27 | 7 | 2.65 |
| | MET exon 14 splice | 7 | 2.65 | 6 | 2.27 |
| KRAS/STK11 and no actionable mutations | | 94 | 35.61 | 70 | 26.52 |

Mutations in KRAS and STK11 are generally mutually exclusive with actionable driver mutations in untreated non-squamous NSCLC [11-13] and their detection could provide additional confidence that patients without actionable alterations are true-negative rather than false-negatives. Combining patients for whom InVisionFirst identified an actionable alteration (18.2% of the cohort) with patients where it did not identify those but identified KRAS and/or STK11 mutations, a total of 142 patients (53.8% of the cohort) had an actionable alteration detected or ruled out. Of the KRAS/STK11 mutations detected in plasma in these patients, 90 had the same variant tested in tissue and 88 of these were detected (97.8% PPV, Table 3). The two mutations not detected in tissue included a KRAS G12C which was observed below the threshold for calling and a mutation in STK11 detected in plasma in a patient who was also KRAS positive by both tissue and plasma. In the 96 patients where InVisionFirst identified mutations in KRAS and/or STK11, tissue data available did not detect any actionable alterations.

Orthogonal Validation by ddPCR

Plasma orthogonal testing by ddPCR revealed an overall concordance of alteration calls of 98.8% (330/334) with PPV of 95.7% and NPV of 99.1% when considering ddPCR as the reference. Discordance was observed in 4 alterations: EGFR exon19del (1 case) and KRAS G12C (2 cases) were detected by InVisionFirst but not by ddPCR. In one case EGFR L858R was detected by ddPCR but not by InVisionFirst. Tissue was available in two of these cases and confirmed the presence of one KRAS G12C mutation and the EGFR L858R mutations. Lastly, one KRAS G12A mutation was detected by both the InVisionFirst assay and tissue sequencing but was identified as KRAS G12D by the ddPCR assay.

DISCUSSION

The study described above is believed to be the first prospective validation of a ctDNA NGS platform for molecular stratification of patients with advanced untreated NSCLC.

Using tissue as the reference, concordance for the full 36 genes in the InVisionFirst panel with matched tissue profiling was 97.8%. Considering clinically actionable alterations in 8 genes that can most influence routine clinical patient management, the PPV was 97.8%, 97.1% NPV, 73.9% sensitivity and 99.4% specificity. Of all mutations detected in plasma, 23% had an allele fraction below 0.5%, highlighting the need for highly sensitive assays with strong performance at low allelic frequencies. The InVisionFirst assay has demonstrated excellent sensitivity in analytical validation studies [9], but despite this high level of sensitivity, approximately 23% of these newly diagnosed stage IIIb/IV NSCLC patients had no mutations detected in ctDNA.

High sensitivity should be coupled with high specificity to ensure that false positive results do not lead to inappropriate therapy. Across the full panel, the PPV was 83.0%, compared to 100% for actionable driver alterations only, the difference being a consequence of 32 non-actionable variants detected in plasma but not in tissue. In 6 of these cases, there was evidence for the variant below thresholds required for calling in tissue. 16 of the remaining 26 calls were TP53 variants. These may be sub-clonal events that only occur at low levels or may be completely absent from the biopsy site. The over-representation of TP53 in ctDNA may also be explained by clonal hematopoiesis [14]. Of note, where tissue was available, all clinically actionable alterations detected by InVisionFirst in plasma were confirmed by tissue profiling. This provides reassurance of the high specificity of the assay and is supported by previous studies of InVisionFirst in NSCLC [15, 16].

In total, 18.2% of patients tested by InVisionFirst had an actionable change detected. An additional 35.6% were found to have a genomic alteration generally mutually exclusive with such actionable alterations. 53.8% of patients therefore had an informative result that could prevent the need for additional invasive biopsies. The strength of this 'rule out' classification was confirmed by the absence of any actionable alterations detected in available tissue in these patients.

Despite excitement regarding ctDNA NGS platforms, there are currently no robust studies in an equivalent clinical setting to provide comparisons across assays. Since ctDNA levels vary between patients at different stages of disease [7], sensitivity is affected by the population in the study. Compared to newly diagnosed patients studied here, the clinical sensitivity of InVisionFirst in previous studies was higher in the relapse setting, with 100% sensitivity (compared to tissue) reported for the EGFR driver mutation at relapse in 30 TKI treated NSCLC patients [16]. Another assay was also reported to have sensitivities ranging from 35.7% to 90.3% in different disease settings [17-19]. Taken together, these observations dictate that clinical validation of assays should be performed in unselected patients from the intended use population with clinical characteristics consistent with the proposed clinical indication prior to clinical adoption [20].

The clinical sensitivity of the InVisionFirst assay demonstrated here is comparable to published data on the FDA approved Roche CobasV2 single-gene EGFR ctDNA assay [21]. Such single-gene tests only identify the small subset of patients with mutations in those genes and are inconclusive for the great majority of patients who potentially require additional testing. The InVisionFirst assay provides data across a panel of genes and can provide a definitive result in >50% of patients through a rule-in/rule-out approach.

Tissue testing for the most common alterations was only successful in 62% of patients in the study, consistent with statistics reported in a recent study across community oncology institutions [3]. Full CGP was successful in significantly fewer patients. Routine implementation of ctDNA testing by InVisionFirst could help to increase the proportion of patients eligible for targeted therapies. Within this study, InVisionFirst identified 48 actionable alterations compared to 38 that were detected by standard of care tissue testing supplemented by CGP. Nearly half of the alterations detected by InVisionFirst were in patients who were not profiled for the alteration due to limitations in tissue testing. This increased detection of actionable alterations would be delivered while reducing costs, patient discomfort and complications associated with repeated invasive tissue biopsies.

Patients with advanced NSCLC progress rapidly and the time taken to obtain results of molecular profiling is therefore paramount. Results for the InVisionFirst assay are now routinely available in 7-days from blood draw. Utilization of such testing early in the work-up of patients with advanced NSCLC may therefore enable earlier therapeutic intervention.

REFERENCES

1. Molina J R, Yang P, Cassivi S D et al. Non-Small Cell Lung Cancer: Epidemiology, Risk Factors, Treatment, and Survivorship. Mayo Clin. Proc. 2008; 83(5):584-594.
2. Noone A M, Howlader N, Krapcho M et al. SEER Cancer Statistics Review, 1975-2015, 2018.
3. Gutierrez M E, Choi K, Lanman R B et al. Genomic Profiling of Advanced Non-Small Cell Lung Cancer in Community Settings: Gaps and Opportunities. Clin. Lung Cancer 2017; 18(6):651-659.
4. Heerink W J, de Bock G H, de Jonge G J et al. Complication rates of CT-guided transthoracic lung biopsy: meta-analysis. Eur. Radiol. 2017; 27(1):138-148.
5. Lokhandwala T, Bittoni M A, Dann R A et al. Costs of Diagnostic Assessment for Lung Cancer: A Medicare Claims Analysis. Clin. Lung Cancer 2017; 18(1):e27-e34.
6. Aisner D L, Bauman J, Chase Cancer Center Joe Chang F Y et al. NCCN Clinical Practice Guidelines in Oncology Version 4.2018 Non-Small Cell Lung Cancer. 2018.
7. Bettegowda C, Sausen M, Leary R J et al. Detection of Circulating Tumor DNA in Early- and Late-Stage Human Malignancies. Sci. Transl. Med. 2014; 6(224):224ra24-224ra24.
8. Odegaard J I, Vincent J J, Mortimer S et al. Validation of a plasma-based comprehensive cancer genotyping assay utilizing orthogonal tissue- and plasma-based methodologies. Clin. Cancer Res. 2018:clincanres.3831.2017.
9. Plagnol V, Woodhouse S, Howarth K et al. Analytical validation of a next generation sequencing liquid biopsy assay for high sensitivity broad molecular profiling. PLoS One 2018; 13(3):e0193802.
10. Gale D, Lawson A R J, Howarth K et al. Development of a highly sensitive liquid biopsy platform to detect clinically-relevant cancer mutations at low allele fractions in cell-free DNA. PLoS One 2018; 13(3):e0194630.
11. Koivunen J P, Kim J, Lee J et al. Mutations in the LKB1 tumour suppressor are frequently detected in tumours from Caucasian but not Asian lung cancer patients. Br. J. Cancer 2008; 99(2):245-252.
12. Ding L, Getz G, Wheeler D A et al. Somatic mutations affect key pathways in lung adenocarcinoma. Nature 2008; 455(7216):1069-1075.
13. Tam I Y S, Chung L P, Suen W S et al. Distinct epidermal growth factor receptor and KRAS mutation patterns in non-small cell lung cancer patients with different tobacco exposure and clinicopathologic features. Clin. cancer Res. 2006; 12(5):1647-53.
14. Hu Y, Ulrich B, Supplee J et al. False positive plasma genotyping due to clonal hematopoiesis. Clin. Cancer Res. 2018:clincanres.0143.2018.

15. Remon J, Caramella C, Jovelet C et al. Osimertinib benefit in EGFR-mutant NSCLC patients with T790M-mutation detected by circulating tumour DNA. Ann. Oncol. 2017; 28(4):mdx017.
16. Guibert N, Hu Y, Feeney N et al. Amplicon-based next-generation sequencing of plasma cell-free DNA for detection of driver and resistance mutations in advanced non-small cell lung cancer. Ann. Oncol. 2018; 29(4): 1049-1055.
17. Chae Y K, Davis A A, Carneiro B A et al. Concordance between genomic alterations assessed by next-generation sequencing in tumor tissue or circulating cell-free DNA. Oncotarget 2016; 7(40):65364-65373.
18. Zill O A, Greene C, Sebisanovic D et al. Cell-Free DNA Next-Generation Sequencing in Pancreatobiliary Carcinomas. Cancer Discov. 2015; 5(10):1040-1048.
19. Chae Y K, Davis A A, Jain S et al. Concordance of Genomic Alterations by Next-Generation Sequencing in Tumor Tissue versus Circulating Tumor DNA in Breast Cancer. Mol. Cancer Ther. 2017; 16(7):1412-1420.
20. Merker J D, Oxnard G R, Compton C et al. Circulating Tumor DNA Analysis in Patients With Cancer: American Society of Clinical Oncology and College of American Pathologists Joint Review. J. Clin. Oncol. 2018: JCO.2017.76.867.
21. Roche Molecular Systems. cobas EGFR Mutation Test v2, 2016.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. ctDNA analysis) those skilled in the art will recognize that its usefulness is not limited thereto and that the present invention can be beneficially utilized in any number of environments and implementations where it is desirable to examine cfDNA, Accordingly, the claims set forth below should be construed in view of the full breadth and spirit of the invention as disclosed herein.

What is claimed is:

1. A method of treatment, comprising:
   (a) performing or having performed a sequencing assay on cell-free DNA (cfDNA) isolated from the blood of a patient that has colorectal cancer, wherein the sequencing assay targets one or more mutations in KRAS and one or more actionable and non-actionable sequence variations in one or more target genes, wherein:
      (i) an actionable sequence variation is a sequence variation for which there is a therapy that targets the protein encoded by the gene having the sequence variation; and
      (ii) a non-actionable sequence variation is a sequence variation for which there is no therapy that targets the protein having the sequence variation;
   (b) determining that the cfDNA has no mutations in KRAS and one or more non-actionable sequence variations by analyzing the results of step (a); and
   (c) administering an epidermal growth factor (EGFR) inhibitor to the patient based on the determination of step (b),
   wherein the decision to administer the EGFR inhibitor is made without considering data obtained from a tumor biopsy.

2. The method of claim 1, wherein the one or more mutations in KRAS comprise mutations selected from the group consisting of the G12A, G12C, G12D, G12F, G12I, G12R, G12S, G12V, G13C, G13D, G13R, GQ60-61GK, Q61H, Q61L and Q61R mutations in the KRAS gene.

3. The method of claim 1, wherein the method comprises:
   calculating the allele frequencies of the one or more non-actionable sequence variations identified in step (b); and
   calculating the probability that there are mutations in KRAS based on the allele frequencies of the one or more non-actionable sequence variations.

4. The method of claim 1, wherein the one or more non-actionable sequence variations identified in (b) are in the APC and TP53 genes.

5. The method of claim 1, wherein the EGFR inhibitor comprises cetuximab or panitumumab.

6. The method of claim 1, wherein the one or more actionable sequence variations are activating mutations in the EGFR gene.

7. The method of claim 1, further comprising:
   analyzing white blood cell DNA from the patient;
   determining whether any of the KRAS mutations or non-actionable sequence variations are due to hematopoiesis of indeterminate potential or a germ-line variation; and
   eliminating sequence variations that are due to hematopoiesis of indeterminate potential or a germ-line variation from the analysis of step (b).

8. A method of treatment comprising:
   (a) performing or having performed a sequencing assay on cell-free DNA (cfDNA) isolated from the blood of a patient that has colorectal cancer, wherein the sequencing assay targets one or more mutations in KRAS and one or more actionable and non-actionable sequence variations in one or more target genes, wherein:
   (b) determining whether the cfDNA comprises one or more mutations in KRAS, and one or more actionable and non-actionable sequence variations in one or more target genes by analyzing the results of step (a), wherein:
      (i) an actionable sequence variation is a sequence variation for which there is a therapy that targets the protein encoded by the gene having the sequence variation; and
      (ii) a non-actionable sequence variation is a sequence variation for which there is no therapy that targets the protein having the sequence variation; and
   (c) treating the patient by:
      i. identifying one or more mutations in KRAS in the cfDNA and administering FOLFIRI, FOLFOX or CAPEOX+/−bevacizumab to the patient, or
      ii. identifying no mutations in KRAS and one or more non-actionable sequence variations in the cfDNA and administering an epidermal growth factor (EGFR) inhibitor to the patient;
   wherein the decision to administer the therapy is made without considering data from a tumor biopsy.

* * * * *